United States Patent
Eshel et al.

(10) Patent No.: US 6,849,063 B1
(45) Date of Patent: Feb. 1, 2005

(54) THERMAL TREATMENT APPARATUS

(75) Inventors: Uzi Eshel, Herzelia (IL); J. Graham Crabtree, Herzelia (IL); Jacob Lazarovitz, Hod Hasharon (IL)

(73) Assignee: WIT IP Corporation, Southborough, MA (US)

( * ) Notice: Subject to any disclaimer, the term of this patent is extended or adjusted under 35 U.S.C. 154(b) by 0 days.

(21) Appl. No.: 09/433,952

(22) Filed: Nov. 5, 1999

Related U.S. Application Data

(63) Continuation of application No. 08/632,830, filed on Apr. 16, 1996, now abandoned, which is a continuation-in-part of application No. 08/212,197, filed on Mar. 11, 1994, now Pat. No. 5,549,559.

(51) Int. Cl.[7] .................................................. A61F 7/12
(52) U.S. Cl. ..................................................... 604/113
(58) Field of Search ........................... 604/65, 67, 113; 606/27, 28; 603/113

(56) References Cited

U.S. PATENT DOCUMENTS

| | | | |
|---|---|---|---|
| 827,099 A | 7/1906 | Hofmann | |
| 899,477 A | 9/1908 | Williams | |
| 1,011,606 A | 12/1911 | Fulton | |
| 1,584,464 A | 5/1926 | Maranville | |
| 1,690,995 A | 11/1928 | Pratt | |
| 1,764,838 A | 6/1930 | Horne | |
| 1,786,373 A | 12/1930 | Walker | |
| 1,827,306 A | 10/1931 | Chapman | |
| 1,904,020 A | 4/1933 | Wappler | |
| 2,026,747 A | 1/1936 | Nemzek | 128/255 |
| 2,043,083 A | 6/1936 | Wappler | 128/303.11 |
| 2,074,634 A | 3/1937 | Ackermann | 128/401 |
| 2,077,453 A | 4/1937 | Albright | 128/254 |
| 2,078,786 A | 4/1937 | Wood | 128/401 |
| 2,103,371 A | 12/1937 | Kleckner | 128/401 |
| 2,190,383 A | 2/1940 | Newman | 128/401 |
| 2,190,384 A | 2/1940 | Newman | 128/400 |
| 2,192,768 A | 3/1940 | Cross | 128/401 |
| 2,466,042 A | 4/1949 | Reich et al. | 128/401 |
| 2,693,191 A | 11/1954 | Raiche | 128/349 |

(List continued on next page.)

FOREIGN PATENT DOCUMENTS

| | | |
|---|---|---|
| DE | 895046 | 12/1953 |
| DE | 19540919 | 5/1997 |
| EP | 105 677 | 4/1984 |

(List continued on next page.)

Primary Examiner—Henry Bennett
Assistant Examiner—Sabrina Dagostino
(74) Attorney, Agent, or Firm—Bradley M. Ganz; James L. Wolfe; Ganz Law, PC

(57) ABSTRACT

A temperature-setting device for providing a predetermined temperature to a quantity of fluid circulating therethrough, a thermal treatment apparatus including such device for selectively treating a targeted tissue adjacent a subject's body cavity, and techniques using such thermal treatment apparatus are provided. The temperature-setting device comprises: an electrically conducting tubular element, a housing element for receiving the tubular element; and a transformer electrically connectable to the housing element. The tubular element functions as a resistor and heats the fluid circulating therethrough. Alternatively, the housing element comprises a thermal conducting member disposed within a bath of a cooling substance, the thermal conducting member having a recess for receiving the tubular element. The tubular element may alternately be placed in a housing element functioning as a heater and a housing element functioning as a cooler, thereby alternately heating or cooling the fluid circulating therethrough. The thermal treatment apparatus comprises: a temperature-setting device according to the present invention; a catheter insertable into a subject's body cavity, the catheter including a thermal treating section for thermally treating a targeted tissue; a pump; thermal sensor assemblies; and an air trapping element.

35 Claims, 8 Drawing Sheets

U.S. PATENT DOCUMENTS

| | | | |
|---|---|---|---|
| 2,734,508 A | 2/1956 | Kozinski | 128/401 |
| 2,777,442 A | 1/1957 | Zelano | 128/206 |
| 2,777,445 A | 1/1957 | Hart | 128/303.12 |
| 2,849,001 A | 8/1958 | Oddo | 128/325 |
| 3,045,677 A | 7/1962 | Wallace | 128/349 |
| 3,227,154 A | 1/1966 | Cook | 128/2 |
| 3,369,549 A | 2/1968 | Armao | 128/303.1 |
| 3,417,746 A | 12/1968 | Moore et al. | 128/6 |
| 3,625,793 A | 12/1971 | Sheridan et al. | 156/229 |
| 3,645,265 A | 2/1972 | Majzlin | 128/303.13 |
| 3,811,450 A | 5/1974 | Lord | 128/349 |
| 3,848,607 A | 11/1974 | St. Clair | 128/400 |
| 4,019,515 A | 4/1977 | Kornblum et al. | 128/246 |
| 4,112,943 A | 9/1978 | Adams | 128/24.1 |
| 4,137,922 A | 2/1979 | Leininger et al. | 128/344 |
| 4,143,649 A | 3/1979 | Foti | 128/2 |
| 4,160,455 A | 7/1979 | Law | 128/400 |
| 4,185,948 A | 1/1980 | Maguire | 417/477 |
| 4,244,377 A | 1/1981 | Grams | 128/742 |
| 4,335,726 A | 6/1982 | Kolstedt | 128/400 |
| 4,367,747 A | 1/1983 | Witzel | 128/344 |
| 4,469,103 A | 9/1984 | Barrett | 128/400 |
| 4,552,557 A | 11/1985 | Rangaswamy | 604/96 |
| 4,574,752 A | 3/1986 | Reichert, Jr. et al. | 123/198 |
| 4,610,660 A | 9/1986 | Rosenberg | 604/49 |
| 4,627,837 A | 12/1986 | Gonzalo | 604/101 |
| 4,628,931 A | 12/1986 | Barrett | 128/399 |
| 4,635,621 A * | 1/1987 | Atkinson | 601/161 |
| 4,636,195 A | 1/1987 | Wolinsky | 604/53 |
| 4,655,746 A | 4/1987 | Daniels et al. | 604/53 |
| 4,662,368 A | 5/1987 | Hussein et al. | 128/303.1 |
| 4,671,795 A | 6/1987 | Mulchin | 604/281 |
| 4,672,962 A | 6/1987 | Hershenson | 128/303.1 |
| 4,676,258 A | 6/1987 | Inokuchi et al. | 128/804 |
| 4,686,965 A | 8/1987 | Bonnet et al. | 128/4 |
| 4,686,985 A | 8/1987 | Lottick | 128/344 |
| 4,709,698 A | 12/1987 | Johnston et al. | 128/303.12 |
| 4,710,169 A | 12/1987 | Christopher | 604/104 |
| 4,754,752 A | 7/1988 | Ginsburg et al. | 128/303.12 |
| 4,787,388 A | 11/1988 | Hofmann | 128/344 |
| 4,793,351 A | 12/1988 | Landman et al. | 128/344 |
| 4,793,352 A | 12/1988 | Eichenlaub | 128/399 |
| 4,799,479 A | 1/1989 | Spears | 128/303.1 |
| 4,819,751 A | 4/1989 | Shimada et al. | 128/344 |
| 4,823,812 A | 4/1989 | Eshel et al. | 128/804 |
| 4,824,436 A | 4/1989 | Wolinsky | 604/53 |
| 4,832,691 A | 5/1989 | Witzel | 604/96 |
| 4,860,744 A | 8/1989 | Johnson et al. | 128/303.1 |
| 4,865,047 A | 9/1989 | Chou et al. | 128/784 |
| 4,893,623 A | 1/1990 | Rosenbluth | 606/192 |
| 4,932,938 A | 6/1990 | Goldberg et al. | 604/96 |
| 4,932,956 A | 6/1990 | Reddy et al. | 606/192 |
| 4,946,449 A | 8/1990 | Davis, Jr. | 604/256 |
| 4,950,227 A | 8/1990 | Savin et al. | 604/8 |
| 4,955,859 A | 9/1990 | Zilber | 604/8 |
| 4,967,765 A | 11/1990 | Turner et al. | 128/785 |
| 4,973,301 A | 11/1990 | Nissenkorn | 604/8 |
| 4,995,872 A | 2/1991 | Ferrara | 604/280 |
| 5,007,437 A | 4/1991 | Sterzer | 428/786 |
| 5,019,075 A | 5/1991 | Spears et al. | 606/7 |
| 5,041,092 A | 8/1991 | Barwick | 604/104 |
| 5,045,056 A | 9/1991 | Behl | 604/49 |
| 5,059,169 A | 10/1991 | Zilber | 604/8 |
| 5,061,241 A | 10/1991 | Stephens, Jr. et al. | 604/114 |
| 5,098,374 A | 3/1992 | Othel-Jacobsen et al. | 604/8 |
| 5,098,379 A | 3/1992 | Conway et al. | 604/51 |
| 5,105,808 A | 4/1992 | Neuwirth et al. | 128/401 |
| 5,112,306 A | 5/1992 | Burton et al. | 604/101 |
| 5,151,100 A | 9/1992 | Abele et al. | 606/28 |
| 5,159,925 A | 11/1992 | Neuwirth et al. | 128/401 |
| 5,163,906 A | 11/1992 | Ahmadi | 604/101 |
| 5,176,626 A | 1/1993 | Soehendra | 604/8 |
| 5,188,596 A | 2/1993 | Condon et al. | 604/101 |
| 5,195,965 A | 3/1993 | Shantha | 604/54 |
| 5,220,927 A | 6/1993 | Astrahan et al. | 128/785 |
| 5,234,004 A | 8/1993 | Hascoet et al. | 607/116 |
| 5,257,977 A * | 11/1993 | Eshel | 604/113 |
| 5,269,758 A | 12/1993 | Taheri | 604/96 |
| 5,269,802 A | 12/1993 | Garber | 606/191 |
| 5,281,213 A | 1/1994 | Milder et al. | 606/15 |
| 5,306,241 A | 4/1994 | Samples | 604/54 |
| 5,312,343 A | 5/1994 | Krog et al. | 604/101 |
| 5,312,430 A | 5/1994 | Rosenbluth et al. | 606/192 |
| 5,314,443 A | 5/1994 | Rudnick | 606/192 |
| 5,322,501 A | 6/1994 | Mahmud-Durrani | 604/8 |
| 5,328,471 A | 7/1994 | Slepian | 604/101 |
| 5,372,600 A | 12/1994 | Beyar et al. | 606/108 |
| 5,391,196 A | 2/1995 | Devonec | 607/96 |
| 5,419,763 A | 5/1995 | Hildebrand | 604/54 |
| 5,431,648 A | 7/1995 | Lev | 606/27 |
| 5,437,673 A * | 8/1995 | Baust | 606/23 |
| 5,439,446 A | 8/1995 | Barry | 604/96 |
| 5,451,218 A | 9/1995 | Moore | 604/317 |
| 5,476,444 A * | 12/1995 | Keeling et al. | 604/4 |
| 5,478,349 A | 12/1995 | Nicholas | 606/198 |
| 5,480,417 A | 1/1996 | Hascoet et al. | 607/101 |
| 5,496,311 A | 3/1996 | Abele et al. | 606/28 |
| 5,499,994 A | 3/1996 | Tihon et al. | 606/192 |
| 5,509,929 A | 4/1996 | Hascoet et al. | 607/101 |
| 5,514,092 A | 5/1996 | Forman et al. | 604/101 |
| 5,514,178 A | 5/1996 | Torchio | 623/12 |
| 5,518,498 A | 5/1996 | Lindenberg et al. | 600/30 |
| 5,527,336 A | 6/1996 | Rosenbluth et al. | 606/192 |
| 5,549,559 A * | 8/1996 | Eshel | 604/113 |
| 5,588,965 A | 12/1996 | Burton et al. | 604/101 |
| 5,609,583 A | 3/1997 | Hakki et al. | 604/282 |
| 5,685,847 A | 11/1997 | Barry | 604/96 |
| 5,702,358 A * | 12/1997 | Witherspoon | 604/61 |
| 5,718,686 A | 2/1998 | Davis | 604/101 |
| 5,746,717 A * | 5/1998 | Aigner | 604/102 |
| 5,752,971 A | 5/1998 | Rosenbluth et al. | 606/192 |
| 5,766,209 A | 6/1998 | Devonec | 604/8 |
| 5,785,641 A | 7/1998 | Davis | 600/30 |
| 5,836,951 A | 11/1998 | Rosenbluth et al. | 606/108 |
| 5,843,144 A | 12/1998 | Rudie et al. | 607/101 |
| 5,876,417 A | 3/1999 | Devonec et al. | 606/192 |
| 5,876,517 A | 3/1999 | Jeannier | 148/264 |
| 5,916,195 A | 6/1999 | Eshel et al. | 604/96 |
| 6,048,358 A * | 4/2000 | Barak | 606/213 |
| 6,228,048 B1 * | 5/2001 | Robbins | 604/31 |
| 6,264,680 B1 * | 7/2001 | Ash | 607/106 |

FOREIGN PATENT DOCUMENTS

| | | |
|---|---|---|
| EP | 341 988 B1 | 11/1989 |
| EP | 543 309 A1 | 5/1993 |
| EP | 672 401 A2 | 9/1995 |
| EP | 672 401 A3 | 9/1995 |
| EP | 733 379 A1 | 9/1996 |
| EP | 753 289 A1 | 1/1997 |
| EP | 790 041 A2 | 8/1997 |
| FR | 439636 | 6/1912 |
| FR | 774318 | 12/1951 |
| GB | 287772 | 3/1928 |
| GB | 315971 | 7/1929 |
| GB | 317604 | 8/1929 |
| GB | 1510004 | 2/1976 |
| GB | 2069063 | 8/1981 |
| JP | 52-104397 | 1/1977 |
| JP | S56-16437 | 2/1981 |
| JP | 60235940 A | 9/1984 |
| JP | 62005045 A | 1/1985 |

| | | | | | | |
|---|---|---|---|---|---|---|
| JP | 61-89330 | 5/1986 | | WO | WO93/04727 | 3/1993 |
| JP | 6343661 | 2/1988 | | WO | WO94/10948 | 5/1994 |
| JP | 63-222759 | 9/1988 | | WO | pct/fr95/00869 | 6/1995 |
| JP | 263440 | 10/1989 | | WO | WO98/00192 | 1/1998 |
| WO | WO91/12846 | 9/1991 | | | | |
| WO | WO92/04934 | 4/1992 | | | | |

\* cited by examiner

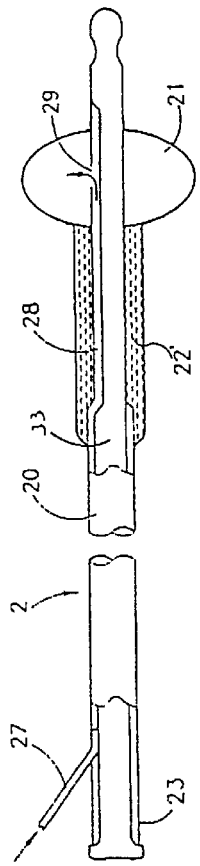
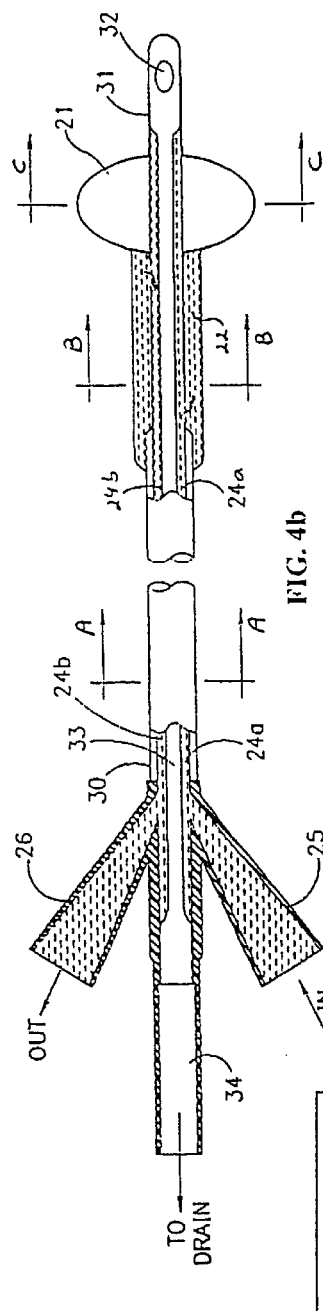
FIG. 4a
FIG. 4b
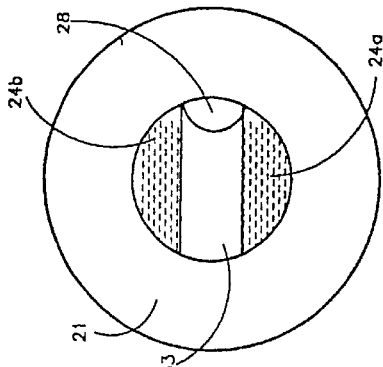
FIG. 5C
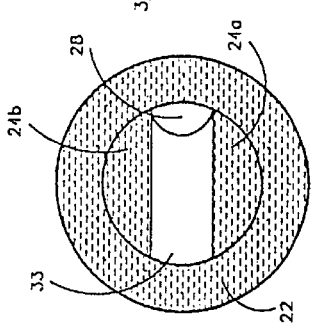
FIG. 5B
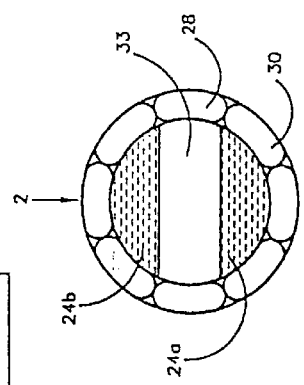
FIG. 5a

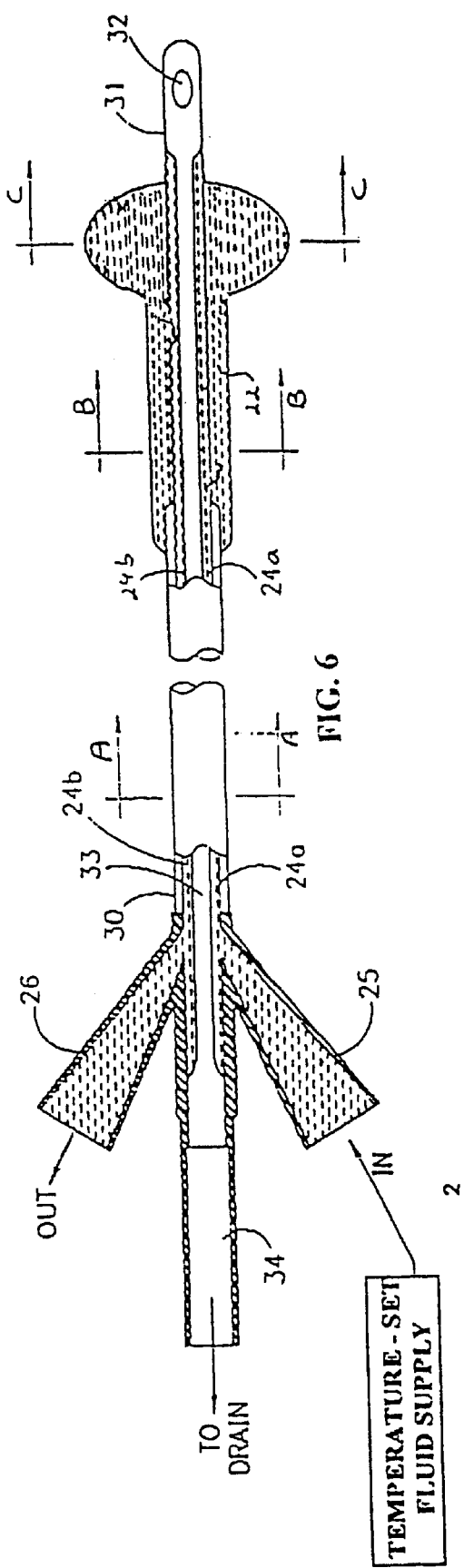
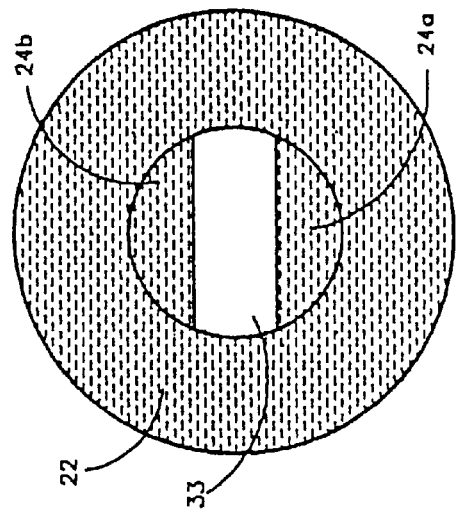
FIG. 6
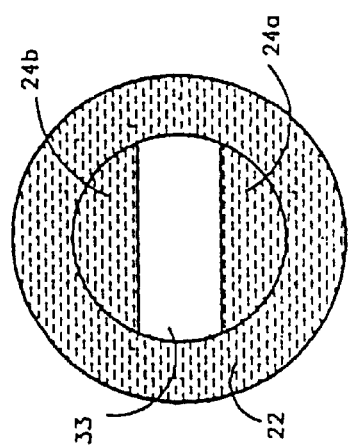
FIG. 7c
FIG. 7b
FIG. 7a

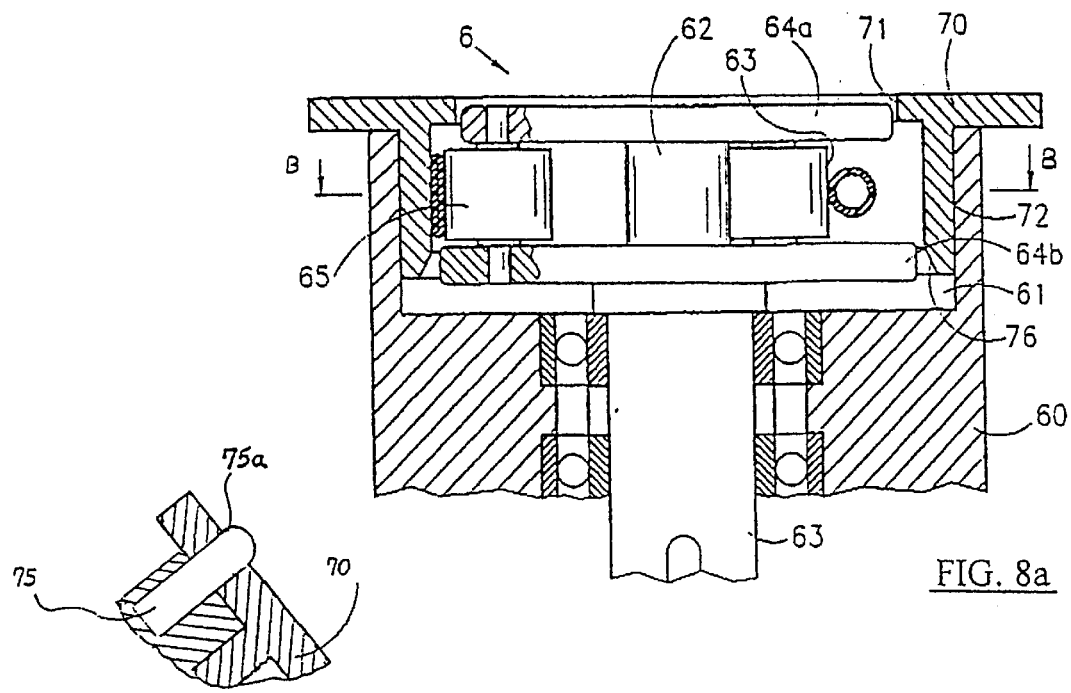
FIG. 8a
FIG. 8c
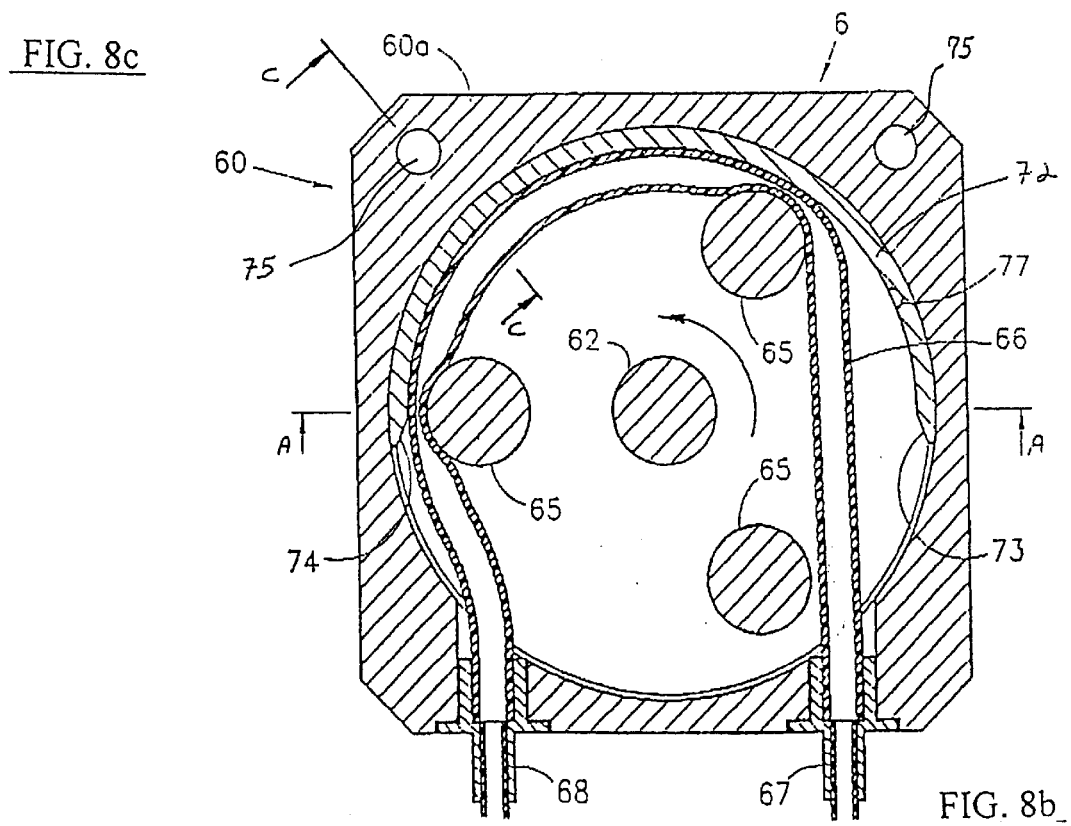
FIG. 8b

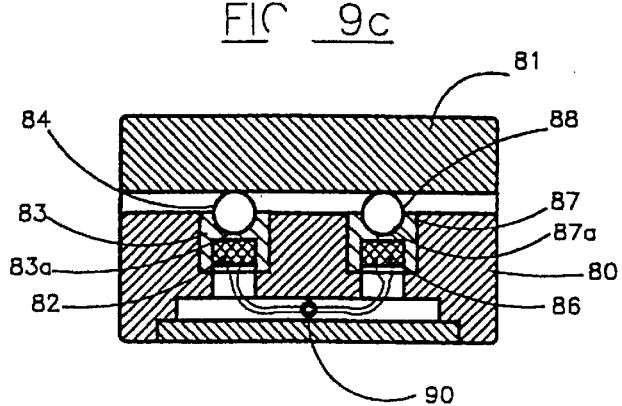
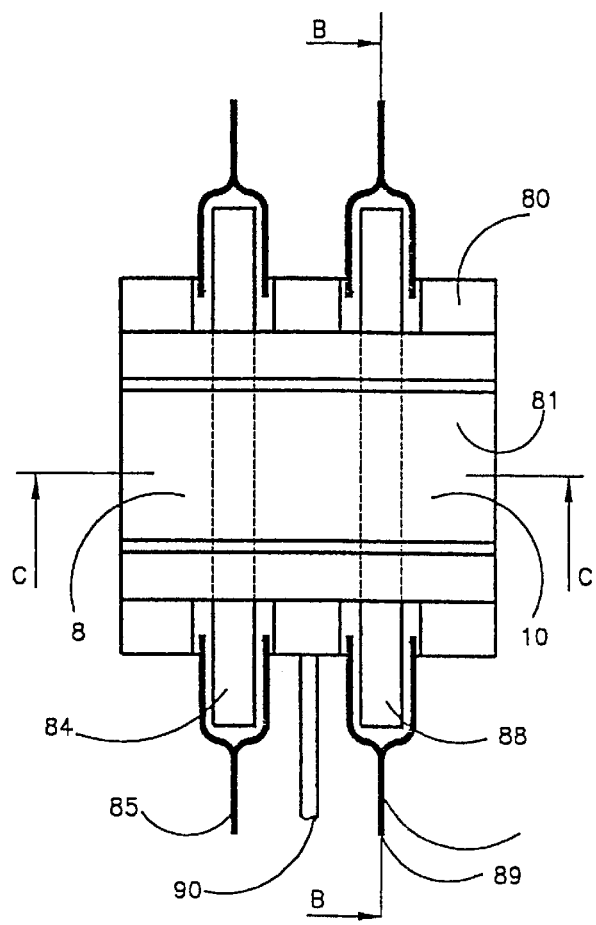
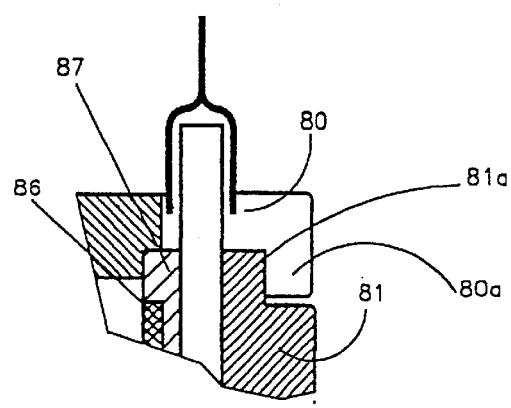

THERMAL TREATMENT APPARATUS

This is a continuation of application Ser. No. 08/632,830 filed Apr. 16, 1996 now abandoned, which is a continuation in part of U.S. patent application Ser. No. 08/212,197, filed Mar. 11, 1994 now U.S. Pat. No. 5,549,559.

FIELD AND BACKGROUND OF THE INVENTION

The present invention relates to a temperature-setting device which can be used to provide a desired temperature to a minimal quantity of fluid circulating in a closed system.

Also the present invention relates to a thermal treatment apparatus including such temperature-setting device for selectively treating a targeted tissue by applying fluid-induced thermal therapy, as disclosed in U.S. Pat. No. 5,257,977 and patent application Ser. No. 08/212,197.

Fluid induced thermal therapy is based on localized heating of a targeted tissue to a predetermined temperature by means of circulating fluid, while keeping the temperature of adjacent healthy tissues unchanged. Relative to therapy methods which use laser, microwave, radiofrequency and ultrasound to produce heat within a tissue, the fluid-induced thermotherapy allows better control of the temperature and the limits of the treated site.

Alternatively, a thermal treatment apparatus according to the present invention may be used for selectively preserving a portion of a tissue treated by cryosurgery, by selectively heating that portion of the tissue.

Various attempts have been made to provide devices for heating an amount of fluid circulating in a closed systems such as fluid-induced thermal therapy systems. Prior art includes heating bath circulators and a heater based on a container serving as a water reservoir. An example is disclosed in U.S. patent application Ser. No. 08/212,197.

However, such configurations consume a considerable amount of energy, since a large quantity of fluid has to be heated (or cooled). Moreover, a considerable damage may be caused in the event of system's failure, by the leakage of a large quantity of fluid into the body cavity.

There is thus a widely recognized need for, and it would be highly advantageous to have, a device which can provide a desired temperature to a minimal quantity of fluid which circulates in a closed system such as fluid-induced thermal therapy system.

It would be further advantageous to have such device which allows to alternately heat and cool a component of such closed system by alternately placing such component in embodiments of the device functioning as heaters and coolers.

It would be further advantageous to have a thermal treatment apparatus for selectively treating a targeted tissue by fluid-induced thermal therapy, which uses a minimal quantity of circulating fluid and therefore consumes minimal energy for heating (or cooling) the fluid, and minimizes the possible damage in the event of fluid leakage.

SUMMARY OF THE INVENTION

According to the present invention there is provided a temperature-setting device for providing a predetermined temperature to a minimal quantity of fluid circulating therethrough, comprising: (a) a tubular element having a relatively low electrical conductivity for receiving a quantity of circulating fluid; (b) a housing element for receiving and anchoring said tubular element therein, and for electrically connecting the tubular element to an electrical circuit; and (c) a transformer element electrically connectable to the electrical circuit.

According to further features in preferred embodiments of the invention described below, the tubular element has two ends connectable to electrically and thermally insulating tubular elements.

Further, the housing element includes fastening elements, comprising: a connector member having a relatively good electrical conductivity, connectable to an electrical circuit; and fastening member for anchoring the tubular member between the fastening member and the connector member.

According to still further features in the described preferred embodiments, the temperature-setting device may include a sensor for sensing the temperature of the tubular element.

The sensor and the transformer element may be electrically connected to a controller. In such configuration, the controller may control the duty cycle of the transformer according to the temperature sensed by the sensor. Alternatively, the controller may interrupt the operation of the transformer and the electrical circuit upon over-heating of the tubular element.

The tubular element and the insulating tubular elements may be disposable.

According to another embodiment, the housing element comprises a thermal conducting member disposed within a bath of a cooling substance, the thermal conducting member featuring a recess for receiving the tubular element therein. The recess preferably defines a lowered area relative to the surface of the cooling substance, for trapping cold air. The recess may be used for receiving a small quantity of fluid for improving the thermal coupling between the thermal conducting member and the tubular element.

According to further features of this embodiment, the thermal conducting member features extensions for increasing the area of contact between the thermal conducting member and the cooling substance.

The tubular element may alternately be place in embodiments functioning as heaters and embodiments functioning as coolers, thereby alternately heating and cooling the fluid circulating therethrough.

According to yet another embodiment, the housing element is in the form of two thermal conducting plates, each of which controllably connectable to a heating and/or cooling source such as a peletier heat pump element.

Each of the thermal conducting plates may feature a recess, the recesses defining a tunnel for receiving the tubular element therein, preferably under pressure.

The thermal conducting plates may alternately heat and cool the tubular element, thereby alternately heating and cooling the fluid circulating therethrough.

Also according to the present invention there is provided a thermal treatment apparatus which uses fluid-induced thermal therapy for selectively treating a targeted tissue adjacent to a subject's body cavity. The thermal treatment apparatus comprises a closed system of circulating fluid and a controller for controlling the closed system, the closed system including: (a) a temperature-setting device according to the present invention; (b) a catheter insertable into a body cavity, the catheter connectable to the temperature-setting device and including a thermal treating section for thermally treating a targeted tissue adjacent the body cavity by circulating fluid of a predetermined temperature through the thermal treating section; (c) a pump for pumping the fluid of predetermined temperature through the closed system; and (d) thermal sensor assembly for sensing the temperature of fluid circulating into the catheter.

According to further features in preferred embodiments of the invention described below, the thermal treatment apparatus may further include a second thermal sensor assembly for sensing the temperature of fluid circulating out of the catheter.

According to still further features in preferred embodiments of the invention described below, the thermal treatment apparatus may include an air trapping element, for trapping air circulating in the system.

The present invention successfully addresses the shortcomings of the presently known configurations by providing a temperature-setting device for providing a predetermined temperature to a minimal quantity of fluid circulating in a closed system.

Further, the present invention provides a thermal treatment apparatus for selectively treating a targeted tissue by fluid-induced thermal therapy, comprising a closed system of circulating fluid which uses a minimal quantity of fluid and therefore consumes minimal energy for heating (or cooling) the fluid, and minimizes the possible damage in the event of fluid leakage; and which further uses temperature control which is completely external to the patien't body.

The present invention discloses a novel temperature-setting device which allows to alternately heat and cool a component of such closed system, the component being in the form of a tubular element having relatively good thermal conductivity, by alternately placing the component in embodiments of the device functioning as heaters and embodiments functioning as coolers.

BRIEF DESCRIPTION OF THE DRAWINGS

The invention is herein described, by way of example only, with reference to the accompanying drawings, wherein:

FIG. 3b is a top view of the embodiment shown in FIG. 3a.

FIG. 4a is a side view, partially in longitudinal section, of a catheter according to the present invention;

FIG. 4b is a side view, partially in longitudinal section, of the catheter illustrated in FIG. 4a rotated 90°.

FIGS. 5a, 5b and 5c are transverse sectional views of the catheter shown in FIG. 4b, along lines A—A, B—B and C—C.

FIG. 6 is a side view, partially in longitudinal section, of another embodiment of a catheter according to the present invention, in which the anchoring section is an integral part of the thermal treating section;

FIGS. 7a, 7b and 7c are transverse sectional views of the catheter shown in FIG. 6, along lines A—A, B—B and C—C.

FIG. 8a is a longitudinal sectional view of a peristaltic pump according to the present invention, along line A—A in FIG. 8b;

FIG. 8b is a transverse sectional view of the peristaltic pump shown in FIG. 8a, along line B—B;

FIG. 8c is a fragmentary detail view along line C—C in FIG. 8b;

FIG. 9a is a top view of an embodiment of a thermal sensor assembly according to the present invention.

FIG. 9b is a fragmentary detail view of the thermal sensor assembly shown in FIG. 9a, along line B—B.

FIG. 9c is a transverse sectional view of the thermal sensor assembly shown in FIG. 9a, along line C—C.

DESCRIPTION OF THE PREFERRED EMBODIMENTS

The present invention is of a temperature-setting device for providing a desired temperature to a minimal quantity of fluid circulating in a closed system.

Also the present invention is of a thermal treatment apparatus including such device, for selectively treating a targeted tissue by fluid-induced thermal therapy using a minimal quantity of circulating fluid and consuming minimal energy for heating (or cooling) the fluid.

The principles and operation of a temperature-setting device according to the present invention and of a thermal treatment apparatus including such device may be better understood with reference to the drawings and the accompanying description.

Figure 1:
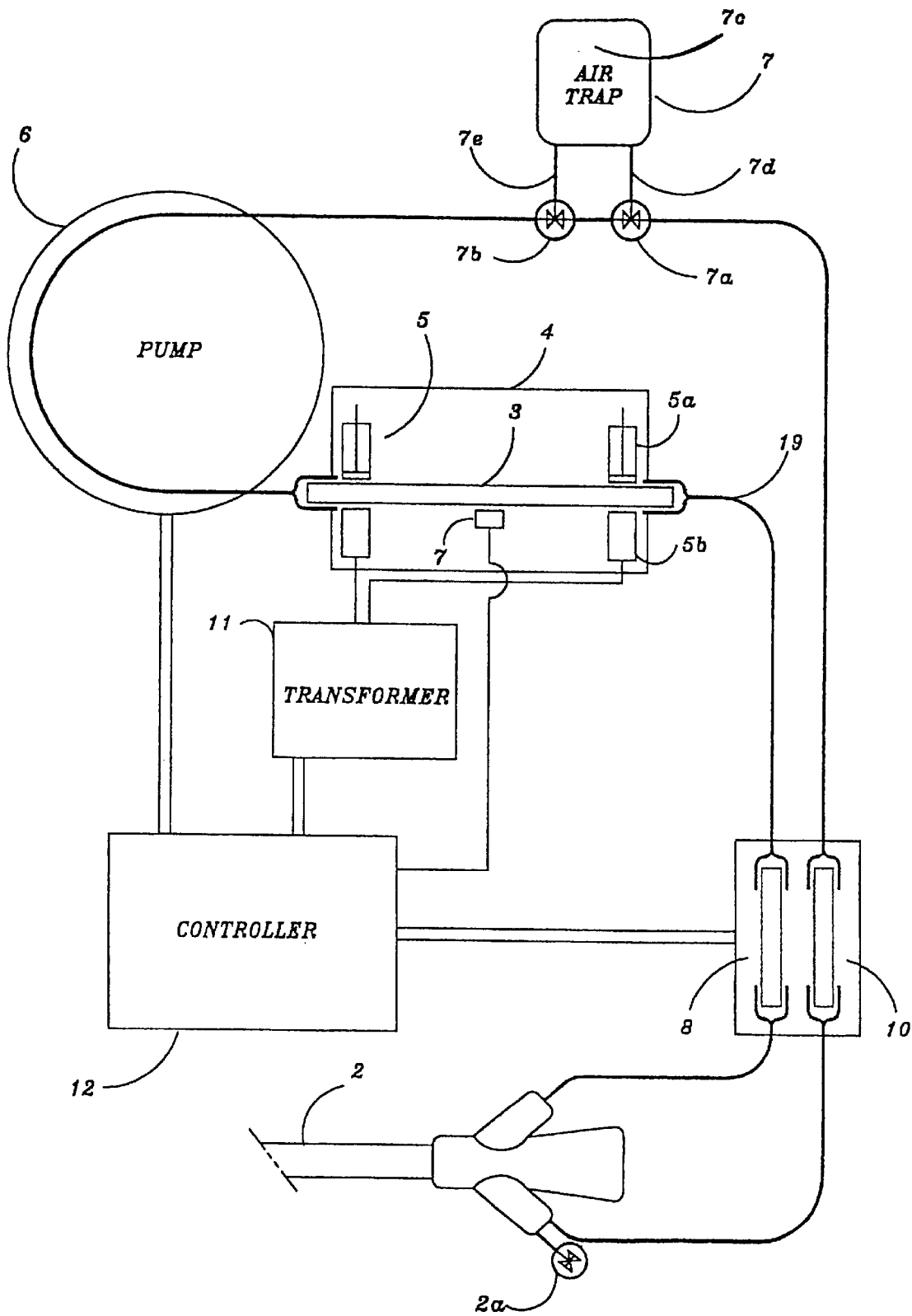
FIG. 1 is a schematic diagram illustrating an embodiment of a temperature-setting device and other main components of a thermal treatment apparatus according to the present invention.

FIG. 1 illustrates a thermal treatment apparatus which uses fluid-induced thermal therapy for selectively treating a targeted tissue adjacent a subject's body cavity. The thermal treatment apparatus comprises a closed system, including: a temperature-setting device 4 for providing a desired temperature to a minimal quantity of fluid circulating through the system; a catheter 2 insertable into the subject's body cavity and connectable to temperature-setting device 4; a pump 6 for pumping the fluid through the system, the pump connectable to temperature-setting device 4; and preferably two thermal sensor assemblies 8 and 10 for measuring the temperature of fluid circulating into and out of catheter 2, respectively. Preferably, the closed system further includes an air trapping element 7 for trapping air circulating in the closed system.

The thermal treatment apparatus further includes a controller 12 for controlling the operation of temperature-setting device 4 and pump 6, preferably according to the temperature sensed by thermal sensor assemblies 8 and 10.

As shown in FIG. 1, a temperature-setting device according to the present invention includes a resistive tubular element 3 having relatively low electrical conductivity and good thermal conductivity. Tubular element 3 may be made, for example, of stainless steel. Tubular element 3 is preferably disposable.

Preferably, temperature-setting device 4 further includes a housing element (not shown) having a recess for receiving tubular element 3. The housing element preferably includes two fastening elements 5 for mechanically anchoring tubular element 3 in the housing element, and electrically connecting the ends of tubular element 3 to a transformer 11. Each of fastening elements 5 comprises two components 5a and 5b. Component 5a preferably includes a fatening member such as a screwing element for anchoring tubular element 3 between component 5a and component 5b. Component 5b has relatively good electrical conductivity for allowing electrical connection between tubular element 3 and transformer 11.

Since tubular element 3 has relatively low electrical conductivity, it functions as a resistor and converts electrical energy to heat, thereby heating the fluid circulating therethrough. This configuration allows to circulate a minimal quantity of heated fluid through the system. Preferably, the quantity of circulating fluid is about 20–50 ml.

The voltage produced by transformer 11 is preferably very low, about 1–5 volts, in order to provide the necessary safety while using the device.

Preferably, temperature-setting device 4 further includes a temperature sensor 92 located at the housing element, for sensing the temperature of tubular element 3. The connection between sensor 7 and tubular element 3 is preferably established readily upon mounting of element 3 in the housing element, under pressure.

Sensor 7 is electrically connected to controller 12. Controller 12 may control the duty cycle of transformer 11 according to the temperature sensed by sensor 7, where the duty cycle refers to the time intervals during which transformer 11 provides electrical current or voltage to the system. Additionally, sensor 7 may function as a safety switch, so that when fluid circulation in the system is interrupted, sensor 7 heats up and consequently controller 12 preferably interrupts the operation of the overall system.

Alternatively, controller 12 may control the duty cycle of transformer 11 according to the temperatute sensed by thermal sensor assemblies 8 and 10.

Figure 2A:
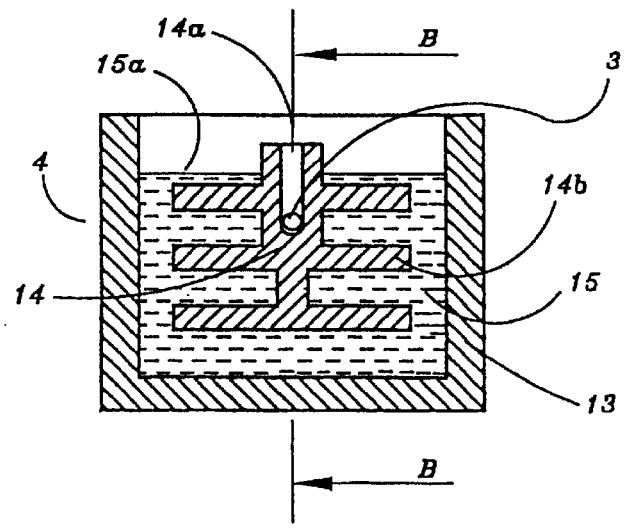
FIG. 2a is a transverse sectional view of another embodiment of a temperature-setting device according to the present invention, along lines A—A in FIG. 2b.
Figure 2B:
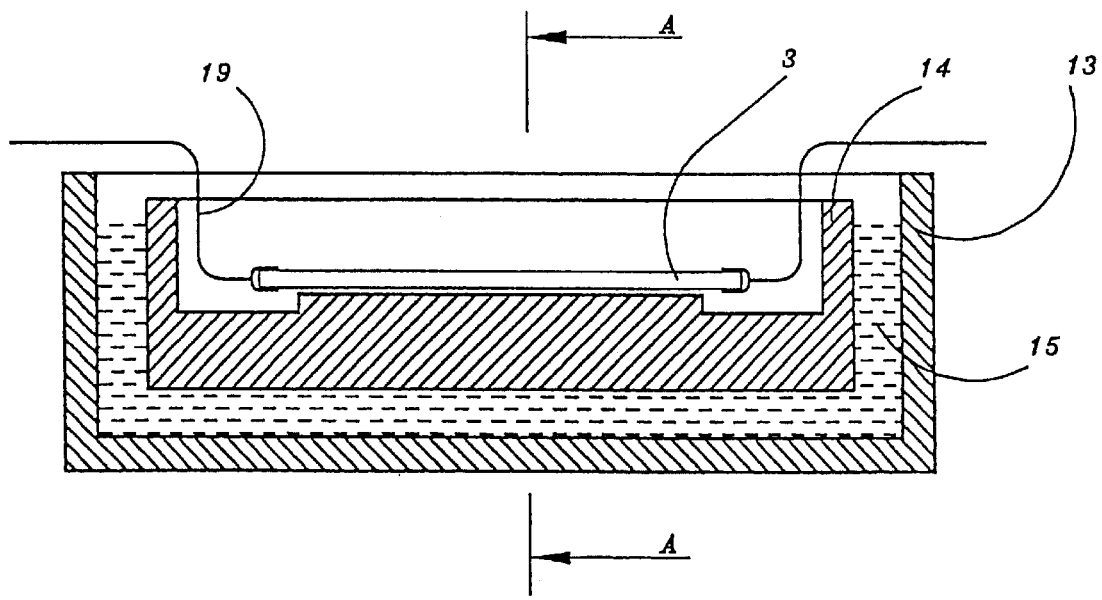
FIG. 2b is a longitudinal sectional view of the embodiment shown in FIG. 2a, along line B—B.

Referring now to FIGS. 2a and 2b, according to another embodiment of temperature-setting device 4, the housing element comprises a thermal conducting member 14 disposed within a bath 13 of a cooling substance 15, such as ice. Thermal conducting member 14 preferably features a recess 14a for receiving tubular element 3 therein. Recess 14a preferably defines a lowered area relative to the surface 15a of cooling substance 15, for trapping cold air. This configuration creates a local well of cold air defined by recess 14a, for efficiently cooling tubular element 3. Further, recess 14a may be used for receiving a quantity of fluid for improving the thermal coupling between thermal conducting member 14b and tubular element 3. Preferably, thermal conducting member 14 further features extensions 14b for increasing the area of contact between thermal conducting member 14 and cooling substance 15. Preferably, the housing element is stored under freezing conditions while not in use.

Temperature-setting device 4 may be used to alternately heat and cool a minimal quantity of fluid circulating through the system, by alternately placing tubular element 3 in embodiments of the device functioning as heaters (e.g. the configuration shown in FIG. 1) and embodiments functioning as coolers (e.g. the configuration shown in FIGS. 2a and 2b). While using the configuration of FIGS. 2a and 2b, transformer 11 is not used.

Figure 3A:
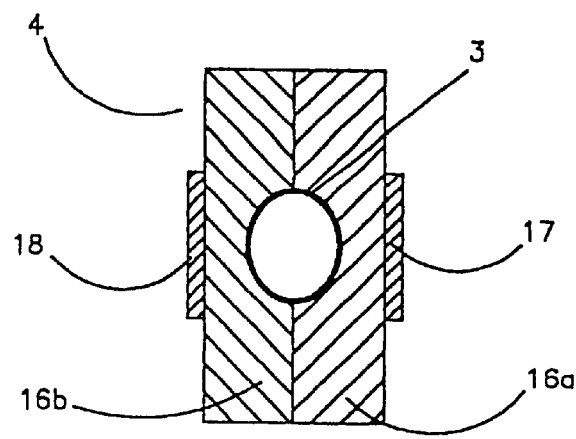
FIG. 3a is a transverse sectional view of yet another embodiment of a temperature-setting device according to the present invention, along lines A—A in FIG. 3b.
Figure 3B:
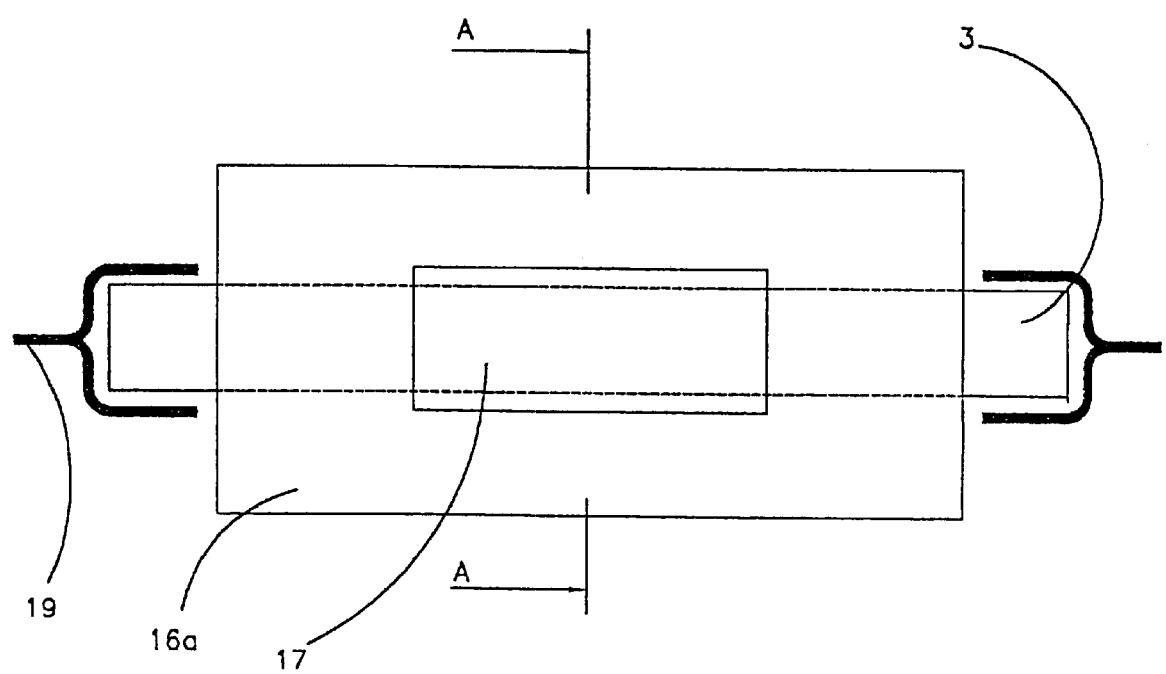

Referring now to FIGS. 3a and 3b, according to yet another embodiment of temperature-setting device 4, the housing element comprises two plates 16a and 16b, made of a material having relatively good thermal conductivity such as aluminum. Plates 16a and 16b are controllably connectable to heating and/or cooling sources 17 and 18, respec- tively. Heating and/or cooling sources 17 and 18 may be, for example, peletier heat pump elements. As shown, each of plates 16a and 16b may feature a recess, the recesses defining a tunnel for receiving tubular element 3 therein, preferably under pressure. This configuration allows better thermal coupling between thermal conducting plates 16a and 16b and tubular element 3.

While using this configuration, tubular element 3 is places within the recess of plate 16b. Plate 16a is then placed on top of plate 16b, covering tubular element 3 so that tubular elenemt 3 is preferably pressed within the tunnel defined by the recesses of plates 16a and 16b.

This configuration may be used as a heater and/or cooler, according to the function (heating or cooling) performed by sources 17 and 18. While using this configuration, transformer 11 is not used.

Referring now to FIGS. 4–7, thermal treatment apparatus according to the present invention further includes a catheter 2 connectable to temperature-setting device 4 and insertable into a subject's body cavity such as urinary bladder, prostatic urethra, uterus and esophagus, for selectively treating a targeted tissue within or near such cavity.

For example, selective treatment of a subject's prostate gland may be accomplished by inserting catheter 2 into the subject's urinary tract and anchoring catheter 2 within the subject's bladder. As shown in FIGS. 4a, 4b and 5a, 5b and 5c, catheter 2 preferably includes a long slender tube 20 formed with an inflatable anchoring section 21 at the proximal end for anchoring the catheter in the subject's body cavity, and thereby locating an inflatable cylindrical thermal treating section 22 near the targeted tissue to be treated. The length of thermal treating section 22 may preferably be adapted according to the distance between the bladder neck and the verumontanum of the particular patient. The distal end of catheter 23 is to be located externally of the subject's body so as to be readily accessible for inflating anchoring section 21 and thermal treating section 22.

A limited quantity of a fluid having a predetermined temperature is circulated through inflatable thermal treating section 22 via two passageways 24a and 24b having an inlet 25 and an outlet 26 at distal end 23 of the catheter. As shown in FIG. 1, a valve member 2a is connected to outlet 26 of the catheter for introducing fluid into the closed system.

Inflatable anchoring section 21 of the catheter is preferably inflated by an amount of unheated fluid introduced via inlet 27 at distal end 23 of the catheter. Inlet 27 preferably communicates with anchoring section 21 via an unheated-fluid passageway 28 and an opening 29.

The portion of the catheter from distal end 23 to inflatable thermal treating section 22 is preferably thermally insulated from the subject's untargeted tissues by means of insulating chambers 30 enclosing passageways 24a and 24b. One of insulating chambers 30 preferably communicates with unheated-fluid passageway 28 through which unheated air is applied to inflate anchoring section 21.

The catheter also includes an extension 31 at the proximal end, which extension is received within the subject's body cavity. Extension 31 is formed with an opening 32 for draining body fluids via draining passageway 33 passing through the length of the catheter and terminating in an outlet 34 attachable to a drain. Alternatively, passageway 33 may be used for introducing a drug into the subject's body cavity. Further, passageway 33 may be used for introducing a stiffening element for facilitating the insertion of the catheter to the subject's body cavity.

Catheter 2 and valve member 2a are preferably disposable.

According to another configuration (not shown), catheter 2 includes only one chamber 30 for communicating with inlet 27 and passageway 28 through which unheated air is applied to inflate anchoring section 21, so that passageways 24a and 24b along slender tube 20 are not insulated.

Yet another configuration of catheter 2 is shown in FIGS. 6 and 7a, 7b and 7c. In this configuration, anchoring section 21 is made as an integral part of thermal treating section 22, and passageway 28 is missing. Further, thermal treating section 22 may feature any geometrical shape, according to the specific geometry of the subject's body cavity. Such configuration may be used, for example, for endometrial ablation, where the geometry of thermal treating section 22 is adapted to fit the specific geometry of a subject's uterus, and insulating chambers 30 enable the use of a heating source for heating the fluid, which is completely external to the subject's body.

According to additional configuration (not shown), anchoring section 21 is made as an integral part of thermal treating section 22, and all of chambers 30, inlet 27 and passageway 28 are missing, so that passageways 24a and 24b along slender tube 20 are not insulated. Inflatable thermal treating section 22 may feature any geometrical shape, according to the specific geometry of the subject's body cavity. Such configuration may be used, for example, for selectively heating a portion of a tissue treated by cryosurgery, thereby preserving that portion.

Referring now to FIGS. 8a, 8b and 8c, thermal treatment apparatus according to the present invention further includes a pump 6 connectable to catheter 2 and temperature-setting device 4. Pump 6 is preferably a peristaltic pump, and includes a housing 60 formed with a cylindrical cavity 61. Disposed within cylindrical cavity 61 is a rotor 62 connected by a drive shaft 63 to a gear motor (not shown) and including a pair of spaced discs 64a, 64b rotatably mounting between them a plurality (3) of rollers 65 within cavity 61. Also located within cylindrical cavity 61 is a peristaltic tube 66 which is engageable by roller 65 for pumping the fluid through the tube during the rotation of rotor 62. Assuming rotor 62 is rotated counter-clockwise in FIG. 8b, the fluid will be pumped through peristaltic tube 66 from an inlet nipple 67 to an outlet nipple 68.

As shown in FIG. 8a, housing 60 further includes a lid 70 with a large central opening 71 for accommodating disc 64a of rotor 62. Lid 70 is formed with a depending skirt 72 which extends into cylindrical cavity 61 such that peristaltic tube 66 is located between the inner surface of skirt 72 and rollers 65. Skirt 72 extends only for a part of the circumference of the lid, e.g., from 160° to 200°, to accomodate the inlet and outlet ends of peristaltic tube 66. As shown in FIG. 8b, skirt 72 extends slightly more than 180°; also, its leading edge 73 and its trailing edge 74 are tapered to provide a gradual application of pressure to the peristaltic tube by roller 65, and a gradual release of the pressure. Peristaltic tube 66 is preferably disposable.

Preferably, housing 60 features two or more pins 75, and lid 70 features two or more depressions 75a respectively for receiving pins 75 therein. Such configuration prevents the rotation of lid 70 during rotation of rotor 62.

The illustrated construction, including depending skirt 72, facilitates the assembly of the peristaltic pump with peristaltic tube 66 between skirt 72 and rollers 65. Thus, with the lid removed peristaltic tube 66 may be conveniently applied around rollers 65. Lid 70 may then be applied with its skirt 72 received between peristaltic tube 66 and the inner surface of cylindrical cavity 61 formed in housing 60, so as to squeeze the tube between skirt 72 and rollers 65. Accordingly, the lower edge of skirt 72 is tapered, as shown at 76 in FIG. 8a, for facilitating the application of the skirt.

The foregoing construction not only facilitates the assembly of the peristaltic pump, but also covers rollers 65 to minimize exposure to a person's fingers or the like. In addition, the thickness of skirt 72 influences the outlet pressure produced by the pump, so that lids 70 with different thickness of skirts 72 may be used to provide different outlet pressures. In addition, the inner surface of skirt 72 may be provided with one or more grooves, as shown at 77 in FIG. 8b, to produce a pulsatile output.

Referring now to FIGS. 9a, 9b, 9c, and 10a, 10b, thermal treatment apparatus according to the present invention preferably includes two thermal sensor assemblies 8 and 10 for measuring the temperature of fluid circularing into and out of catheter 2, respectively. Thermal sensor assemblies 8 and 10 are preferably enclosed within a common housing 80 and closed by a common cover 81. Thermal sensor assembly 8 near the inlet end of catheter 2 includes a thermal sensor element 82 received within a rectangular recess formed in a metal thermal coupling member 83. The opposite face of the coupling member is formed with a recess for receiving a metal tube 84 connectible to an inlet tube 85 near the inlet end of the catheter. Thermal sensor assembly 10 similarly includes a thermal sensor element 86 received within a recess formed in another metal thermal coupling member 87. The opposite face of member 87 is similarly formed with a recess for receiving a metal tube 88 adapted to be coupled to an outlet tube 89 near the outlet end of the catheter. Electrical connections are made to the two thermal sensor elements 82 and 86 via a cable 90 leading to controller 12 in FIG. 1. Metal tubes 84 and 88 and inlet and outlet tubes 85 and 89 are preferably disposable.

The two thermal coupling members 83, 87, as well as the two tubes 84, 88, are of a metal, such as stainless steel, having relatively good thermal conductivity. Coupling members 83, 87 include relatively thin web portions 83a, 87a, respectively, between thermal sensor elements 82, 86 and metal tubes 84, 88, so as to provide a good thermal coupling between the fluid flowing through the two metal tubes and their respective thermal sensor elements. Cover 81, fixed to the common housing 80 in any suitable manner, preferably presses metal tubes 84, 88 firmly against their respective metal coupling members 83, 87.

As shown in FIG. 9b, cover 81 may include extensions 81a, and housing 80 may respectively include depressions 80a for receiving extensions 81a of cover 81. Cover 81 is threaded into the chamber defined by depressions 80a of housing 80, pressing each of metal tubes 84 and 88 firmly against their respective metal coupling members 83 and 87.

Figure 10A:
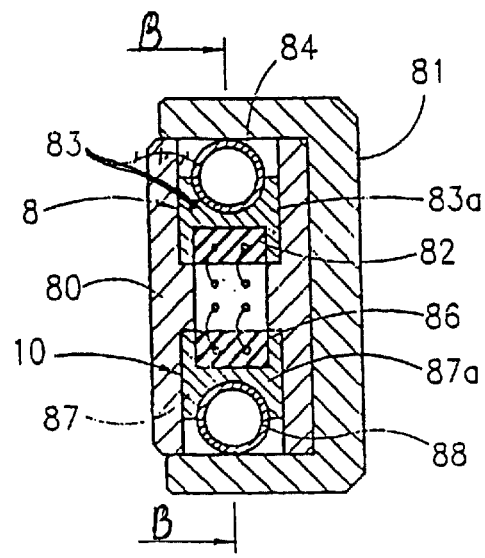
FIG. 10a is a transverse sectional view of another embodiment of a thermal sensor assembly, along line A—A in FIG. 10b.
Figure 10B:
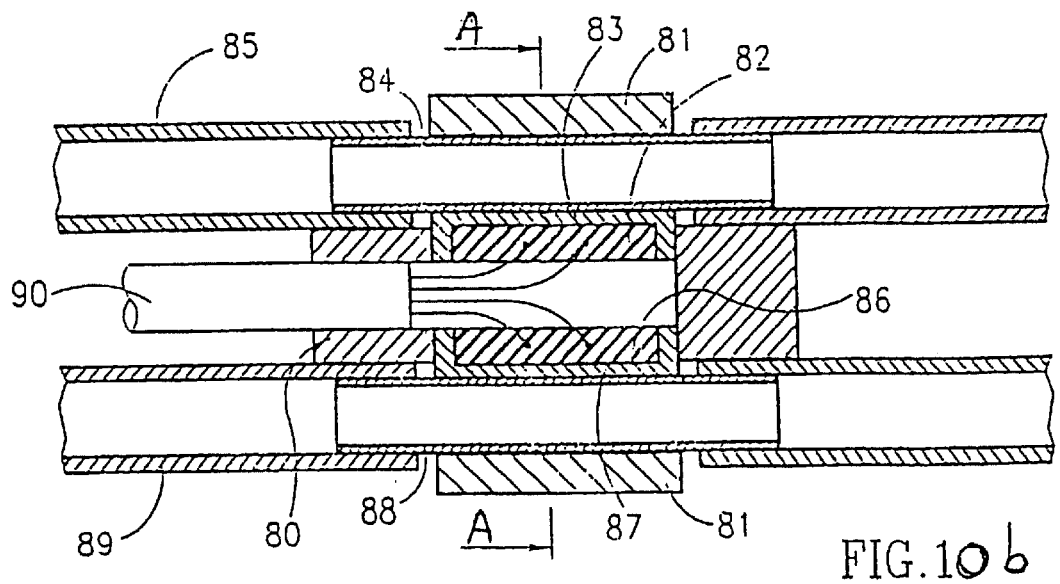
FIG. 10b is a longitudinal sectional view of the thermal sensor assembly shown in FIG. 10a, along line B—B.

Another possible configuration is shown in FIGS. 10a and 10b, wherein housing 80 features the shape of "H", and cover 81 presses each of metal tubes 84 and 88 firmly against their respective metal coupling members 83 and 87, and the central segment of housing element 80. Cover 81 may be fixed to the common H-shaped housing 80 in any suitable manner.

As shown in FIG. 1, thermal treatment apparatus according to the present invention may further include an air trapping element for trapping air circulating in the closed system. Air trapping element 7 may be in the form of a hung container 7c, which is preferably flexible and made of plastic, and controllably connectable to the closed system by means of two tubular elements 7d and 7e, and two valve members 7a and 7b. Container 7c, tubular elements 7d and 7e, and valve members 7a and 7b are preferably disposable.

Valve members 7a and 7b may controllably allow or block fluid circulation into and out of container 7c. When fluid is allowed to circulate through container 7c, the air found in the circulating fluid is trapped within the container.

Air trapping element 7 is preferably used for priming the system.

Thermal treatment apparatus according to the present invention preferably includes a disposable set, including: (a) different configurations of catheter 2 for different types of treatments; and (b) a tubing assembly, including: tubular element 3 of temperature-setting device 4; peristaltic tube 66 of pump 6; metal tubes 84 and 88 of thermal sensor assemblies 8 and 10; air trapping element 7; valve members such as 2a, 7a and 7b; and other tubular elements constituting the closed system of circulating fluid.

The overall operation of a thermal treatment apparatus including a temperature-setting device according to the present invention is as follows:

The configuration of catheter 2 is selected according to the specific type of treatment; catheter 2 is then connected to the disposable tubing assembly; tubular element 3 is placed in a suitable embodiment of temperature-setting device 4; peristaltic tube 66 is placed in pump 6; and metal tubes 84 and 88 are placed within thermal sensor assemblies 8 and 10 respectively.

Valve members 7a and 7b are set to allow circulation of fluid through air trapping element 7, and a minimal quantity (about 20–50 ml) of fluid is then introduced into the closed system via valve member 2a. Priming of the system is then carried out by activating pump 6 and circulating the fluid through air trapping element 7, thereby trapping air found in the system.

Valve members 7a and 7b are then set to block circulation of fluid through air trapping element 7, thereby directing the fluid to circulate through the main tube of the system.

An additional quantity of fluid is added at this stage to inflate thermal treating section 22 to its operational volume, if required.

Pump 6 is then switched off, and a quantity of fluid is pumped out of the system via valve member 2a, in order to deflate thermal treating section 22 and to allow the insertion of catheter 2 into the subject's body cavity.

Referring now to FIGS. 4 and 5, catheter 2 is inserted into a subject's body cavity until inflatable anchoring section 21 at the proximal end passes through the neck of the cavity. An unheated fluid, preferably air, is introduced via inlet 27 and passageway 28 into the interior of anchoring section 21 to inflate it. This anchors section 21 in the subject's body cavity, whereupon heating section 22 of the catheter extends through the targeted tissue to be treated.

The quantity of fluid that was pumped out of the system for deflating thermal treating section 22 is now pumped into the system via valve member 2a for inflating thermal treating section 22 while placed within the subject's body cavity.

Referring now to FIGS. 6 and 7, wherein anchoring section 21 is made as an integral part of thermal treating section 22, and thermal treating section 22 features any geometrical shape. while using this configuration, the quantity of fluid that was pumped out of the system for deflating thermal treating section 22 is now pumped into the system via valve member 2a for inflating thermal treating section 22 while placed within the subject's body cavity. If required, an additional quantity of fluid is pumped into the system via valve member 2a so as to fill the particular body cavity, thereby efficiently heating or cooling the tissues therein.

The fluid is then circulated by peristaltic pump 6 through the closed system including thermal treating section 22 of the catheter and tubular element 3 of the temperature-setting device.

During circulation, tubular element 3 which is electrically connected to transformer 11 (FIG. 1), converts electrical energy to heat, thereby heating the fluid circulating therethrough. Alternatively, tubular element 3 may be placed in the embodiment shown in FIGS. 2a and 2b, thereby cooling the fluid circulating therethrough. Thus, temperature-setting device 4 may be used to alternately heat and cool the fluid circulating in the system by alternately placing tubular element 3 within embodiments of the device functioning as heaters and coolers.

Alternatively, tubular element 3 may be placed in the embodiment shown in FIGS. 3a and 3b, thereby alternately heating and cooling the circulating fluid using the same embodiment.

Sensor assemblies 8 and 10, electrically connected to controller 12, sense the temperature of fluid near the inlet and outlet ends of the catheter, respectively. Controller 12 maintain the desired temperature by controlling the duty cycle of transformer 11, and therefore the heating level of tubular element 3.

Sensor 7, electrically connected to controller 12, senses the temperature of tubular element 3. Controller 12 interrupts the operation of the overall system upon over-heating of tubular element 3.

While using the configurations of catheter 2 shown in FIGS. 4–7, only inflated thermal treating section 22 of the catheter is effective to heat a targeted tissue, because of the thermal insulation provided by the unheated air within insulating chambers 30. While using the configuration shown in FIGS. 4 and 5, the insulation is further provided by anchoring section 21.

Accordingly, the fluid applied to inflatable thermal treating section 22 may be heated to a relatively high tempetature for application to the targeted tissues, with less danger of unduly heating untargeted tissues contacted by the catheter. The inflation of thermal treating section 22 also presses that section firmly against the targeted tissue to be thermally treated thereby further enhancing the heating effects.

Drain opening 32 at the proximal end of the catheter, and passageway 33 through the catheter, provide a drain for body fluids or enable the introduction of drugs into the body cavity.

While the invention has been described with respect to a limited number of embodiments, it will be appreciated that many variations, modifications and other applications of the invention may be made.

What is claimed is:

1. Thermal treatment apparatus for selectively treating a targeted tissue adjacent a subject's body cavity, comprising a closed system of circulating fluid and a controller for controlling said closed system, said closed system including:
 (a) a temperature-setting device for providing a predetermined temperature to a quantity of fluid circulating therethrough, including:
  (i) a tubular element having electrical conductivity and thermal conductivity configured to apply heat to circulating fluid as the circulating fluid flows therethrough, said tubular element having two ends connectable to electrically and thermally insulating tubular elements;
  (ii) a housing element for receiving said tubular element, said housing element including fastening elements, said fastening elements including a connector member having electrical conductivity connectable to an electrical circuit; and (iii) a transformer element operatively associated with said electrical circuit, said transformer element electrically connected to said controller;

(b) a catheter insertable into a body cavity, said catheter in fluid communication with said tubular element of said temperature-setting device, said catheter including a thermal treating section for thermally treating a targeted tissue adjacent said body cavity by circulating fluid of a predetermined temperature through said thermal treating section in a closed loop system, said catheter being disposable;

(c) a pump for pumping said fluid of predetermined temperature through said closed loop system, said pump in fluid communication with said tubular element of said temperature-setting device, said pump electrically connected to said controller; and (d) a thermal sensor assembly for sensing the temperature of fluid circulating into said catheter, said thermal sensor assembly in communication with the fluid that circulates through said catheter, said thermal sensor assembly electrically connected to said controller.

2. The apparatus of claim 1, wherein said apparatus further includes a second thermal sensor assembly for sensing the tempetature of fluid circulating out of said catheter, said second thermal sensor assembly having two ends, one of said ends connectable to said catheter and the other of said ends connectable to said pump by means of said insulating tubular elements, said second thermal sensor assembly electrically connected to said controller.

3. The apparatus of claim 1, wherein said apparatus further includes an air trapping element for trapping air circulating in the system, said air trapping element comprising a hung container connectable to said closed system, said air trapping element being disposable.

4. The apparatus of claim 1, wherein said temperature-setting device further includes a sensor for sensing the temperature of said tubular element, said sensor electrically connected to said controller.

5. The apparatus of claim 4, wherein said controller controls the duty cycle of said transformer element according to the temperature sensed by said sensor.

6. The apparatus of claim 4, wherein said controller interrupts the operation of said transformer element, said electrical circuit and said closed system upon a certain value of temperature sensed by said sensor.

7. The apparatus of claim 4, wherein said housing element of said temperature-setting device features a recess for receiving said tubular element, and a contact between said tubular element and said sensor is established upon mounting of said tubular element in said recess under pressure.

8. Thermal treatment apparatus for selectively treating a targeted tissue adjacent a subject's body cavity, comprising a closed system of circulating fluid and a controller for controlling said closed system, said closed system including:

(a) a temperature-setting device for providing a predetermined temperature to a quantity of fluid circulating therethrough, including:

(i) a tubular element having electrical conductivity and thermal conductivity configured to allow circulating fluid to flow therethrough;

(ii) a housing element for receiving said tubular element, said housing element comprising an electrical circuit operatively associated with said tubular element and a fastening member for anchoring said tubular element therein; and (iii) a transformer element connectable to said electrical circuit, said transformer element electrically connected to said controller;

(b) a catheter insertable into a body cavity, said catheter in fluid communication with said tubular element of said temperature-setting device, said catheter including a thermal treating section for thermally treating a targeted tissue adjacent said body cavity by circulating fluid of a predetermined temperature through said thermal treating section, said catheter being disposable;

(c) a pump for pumping said fluid of predetermined temperature through said closed system, said pump in fluid communication with said tubular element of said temperature-setting device, said pump electrically connected to said controller; and (d) a thermal sensor assembly for sensing the temperature of fluid circulating into and/or out of said catheter, said thermal sensor assembly electrically connected to said controller, wherein the voltage produced in said electrical circuit is between about 1–5 volts.

9. The apparatus of claim 1, wherein said tubular element of said temperature-setting device, said insulating tubular elements and other tubular elements constituting the closed system are disposable.

10. Thermal treatment apparatus for selectively treating a targeted tissue adjacent a subject's body cavity by exchanging heat with said targeted tissue, comprising a closed system of circulating fluid and a controller for controlling said closed system, said closed system including:

(a) a temperature-setting device for providing a predetermined temperature to a quantity of fluid circulating through the closed system; including (i) a tubular element having thermal conductivity for receiving a quantity of circulating fluid; and (ii) a housing element for receiving said tubular element, said housing element configured for exchanging heat with said tubular element, said housing element detachably connectable to said tubular element;

(b) a catheter insertable into a body cavity, said catheter in fluid communication with said tubular element of said temperature-setting device, said catheter including a thermal treating section for thermally treating a targeted tissue adjacent said body cavity by circulating fluid of a predetermined temperature through said thermal treating section, said catheter being disposable;

(c) a pump for pumping said fluid of predetermined temperature through said closed system, said pump in fluid communication with said tubular element of said temperature-setting device, said pump electrically connected to said controller; and (d) a thermal sensor assembly for sensing the temperature of fluid circulating into and/or out of said catheter, said thermal sensor assembly in communication with said tubular element of said temperature-setting device, said thermal sensor assembly electrically connected to said controller.

11. The apparatus of claim 10, wherein said temperature-setting device includes a second housing element for receiving said tubular element, each of said housing elements being detachably connectable to a thermal source, said tubular element being transferable between said housing elements for controllably heating and cooling the fluid circulating therethrough.

12. The apparatus of claim 11, wherein said tubular element features substantially low electrical conductivity, and wherein said housing element includes connectors having substantially good electrical conductivity, said connectors being electrically connected to an electrical circuit, said connectors for receiving said tubular element, and wherein said second housing element is connected to a cooling source.

13. Thermal treatment apparatus for selectively treating a targeted tissue adjacent a subject's body cavity by heating and cooling said targeted tissue, comprising a closed loop system of circulating fluid and a controller for controlling said closed loop system, said closed loop system including:
 (a) a temperature-setting device for heating and cooling a quantity of fluid circulating therethrough, including:
  (i) a tubular element having thermal conductivity for selectively heating a quantity of circulating fluid flowing therethrough, said tubular element having two ends connectable to thermally insulating tubular elements;
  (ii) a housing element for alternately heating and cooling said tubular element, said housing element including two thermal conducting plates, each having a recess, said recesses defining a tunnel for receiving said tubular element under pressure;
  (iii) a heating source detachably connectable to said housing element; and
  (iv) a cooling source detachably connectable to said housing element, said housing element configured for controllably heating and cooling said tubular element, thereby alternately heating and cooling the fluid circulating therethrough;
 (b) a catheter insertable into a body cavity, said catheter connectable to said tubular element of said temperature-setting device by means of said insulating tubular element, said catheter including a thermal treating section for thermally treating a targeted tissue adjacent said body cavity by circulating fluid of a predetermined temperature through said thermal treating section, said catheter being disposable;
 (c) a pump for pumping said fluid of predetermined temperature through said closed loop circulating fluid system, said pump connectable to said tubular element of said temperature-setting device by means of said insulating tubular element, said pump electrically connected to said controller; and
 (d) a thermal sensor assembly for sensing the temperature of fluid circulating into and/or out of said catheter, said thermal sensor assembly comprising a thermal tube having two ends, one of said ends connectable to said catheter and the other of said ends connectable to said tubular element of said temperature-setting device by means of said insulating tubular elements, said thermal sensor assembly electrically connected to said controller.

14. The apparatus of claim 13, wherein said temperature-setting device comprises:
 (a) a tubular element having relatively good thermal conductivity for receiving a quantity of circulating fluid, said tubular element having two ends connectable to thermally insulating tubular elements, said tubular element and said insulating tubular elements being disposable;
 (b) a housing element for alternately heating and cooling said tubular element, said housing element comprising two thermal conducting plates, each having a recess, said recesses defining a tunnel for receiving said tubular element under pressure; and
 (c) peletier heat pump elements detachably connectable to said thermal conducting plates,
 said peletier heat pump elements alternately heating and cooling said thermal conducting plates, thereby alternately heating and cooling the fluid circulating through said tubular element.

15. The apparatus of claim 1, wherein said catheter includes a proximal end formed with an inflatable thermal treating section to be located within the body cavity, and a distal end to be located externally of the body cavity; said catheter being formed with first and second passageways extending from said distal end to said inflatable thermal treating section for circulating fluid of a predetermined temperature through said inflatable thermal treating section.

16. The apparatus of claim 15, wherein said catheter further includes thermal insulation surrounding said first and second passageways from close to said distal end to close to said inflatable thermal section, said thermal insulation including a plurality of separate compartments containing a non-heated fluid, said compartments extending axially along the catheter, thereby the inflatable thermal treating section and the targeted tissue in its proximity may be heated to a desired temperature without correspondingly heating non-targeted tissues.

17. The apparatus of claim 10, wherein said catheter includes a proximal end formed with an inflatabe anchoring section for anchoring the catheter in the body cavity, a distal end to be located externally of the body cavity, and an inflatable thermal treating section adjacent said proximal end to be located near the targeted tissue; said catheter being formed with first and second passageways extending from said distal end to said inflatable thermal treating section for circulating fluid of a predetermined temperature through said inflatable thermal treating section, and a third passageway extending from said distal end to said inflatable anchoring section for introducing unheated fluid into said inflatable anchoring section.

18. The apparatus of claim 17, wherein said catheter further includes thermal insulation surrounding said first and second passageways from close to said distal end to close to said inflatable thermal treating section, said thermal insulation including a plurality of separate compartments containing a non-heated fluid, said compartments extending axially along the catheter, thereby the inflatable thermal treating section and the targeted tissue in its proximity may be heated to a desired temperature without correspondingly heating non-targeted tissues.

19. The apparatus of claim 1, wherein said pump includes:
 (a) a housing formed with a substantially cylindrical cavity having an inner surface, said housing provided with a lid, said lid having a depending skirt removably engageable within said cylindrical cavity so as to form an inset lining around a part of said inner surface;
 (b) a rotor rotatably mounted within said cylindrical cavity, said rotor carrying rollers; and
 (c) a peristaltic tube, said peristaltic tube being disposable, such that, when said depending skirt is not engaged in said cylindrical cavity, the peristaltic tube may be easily inserted between said rollers and said inner surface and, when said depending skirt is engaged in said cylindrical cavity, the peristaltic tube is engaged between said rollers and said inset lining such that rotation of said rotor pumps fluid through the peristaltic tube.

20. Thermal treatment apparatus for selectively treating a targeted tissue adjacent a subject's body cavity, comprising a closed system of circulating fluid and a controller for controlling said closed system, said closed system including:

(a) a temperature-setting device for providing a predetermined temperature to a quantity of fluid circulating therethrough, including:
  (i) a tubular element having electrical conductivity and thermal conductivity for exchanging heat with a quantity of circulating fluid flowing therethrough;
  (ii) a housing element for receiving said tubular element, said housing element including an electrical circuit operatively associate with said tubular element and a fastening member for anchoring said tubular element therein; and
  (iii) a transformer element in communication with said electrical circuit, said transformer element electrically connected to said controller;
(b) a catheter insertable into a body cavity, said catheter in fluid communication with said tubular element of said temperature-setting device, said catheter including a thermal treating section for thermally treating a targeted tissue adjacent said body cavity by circulating fluid of a predetermined temperature through said thermal treating section, said catheter being disposable;
(c) a pump for pumping said fluid of predetermined temperature through said closed system, said pump in fluid communication with said tubular element of said temperature-setting device, said pump electrically connected to said controller; and
(d) a thermal sensor assembly for sensing the temperature of fluid circulating into said catheter, said thermal sensor assembly operatively associated with said tubular element of said temperature-setting device, said thermal sensor assembly electrically connected to said controller, wherein said thermal sensor assembly includes: a thermal sensor; a disposable metal tube connectible to the end of a passageway of the catheter to receive the fluid flowing therethrough; a metal thermal coupling member formed with a recess on one face for receiving the thermal sensor therein, a recess on the opposite face complementary to the shape of the metal tube for receiving the metal tube therein, and a relatively then web between the two recesses; and a cover pressing said metal tube to said thermal coupling member.

21. A closed loop thermal treatment apparatus for a body cavity, comprising:
  (a) a catheter for insertion into the body cavity, said catheter being capable of circulating a quantity of circulating fluid;
  (b) a temperature-setting device for setting a temperature of said fluid being received by said catheter, said temperature-setting device comprising:
    (i) a tubular element, said tubular element being attached to said catheter such that fluid flows through said tubular element to said catheter; and
    (ii) a power source operably associated with said tubular element to supply power to said tubular element such that said tubular element controllably heats the circulating fluid as the fluid flows therethrough; and
  (c) a pump in fluid communication with said tubular element, said pump configured to drive said fluid through said tubular element; and
  (d) an air trap in fluid communication with said circulating fluid for removing air from said circulating fluid.

22. The thermal treatment apparatus of claim 21, wherein said power source comprises a transformer, and wherein said temperature-setting device further comprises:
  (a) a temperature sensor for sensing a temperature of said fluid, said temperature sensor being in communication with said tubular element; and
  (b) a controller for controlling said transformer, said controller being connected to said temperature sensor and to said transformer such that said controller is able to control said transformer to controllably power said tubular element based on a desired target thermal treatment temperature and an actual sensed temperature of said fluid.

23. The thermal treatment apparatus of claim 21, further comprising:
  (d) an inflatable thermal treating section configured to be placed within the body cavity, said inflatable thermal treating section being formed at one end portion of said catheter.

24. The thermal treatment apparatus of claim 23, wherein said catheter further features:
  (i) a first passageway and a second passageway connected to said inflatable thermal treating section such that said fluid flows from said catheter into said inflatable thermal treating section.

25. A thermal treatment apparatus for a body cavity, comprising:
  (a) a catheter for insertion into the body cavity, said catheter being capable of receiving a quantity of circulating fluid, said catheter comprising:
    (i) an inflatable thermal treating section configured to be placed within the body cavity, said inflatable thermal treating section being formed at one end portion of said catheter;
    (ii) a first passageway and a second passageway connected to said inflatable thermal treating section such that said fluid flows from said catheter into said inflatable thermal treating section;
  (b) a temperature-setting device for setting a temperature of said fluid being received by said catheter, said temperature-setting device comprising:
    (i) a tubular element, said tubular element being attached to said catheter such that fluid flows through said tubular element to said catheter; and
    (ii) a transformer electrically connected to said tubular element, said transformer configured to supply power to said tubular element such that said tubular element heats the fluid as the fluid flows therethrough; and
  (c) a pump in fluid communication with said tubular element, said pump configured to drive said fluid through said tubular element; and
  (d) an air trap in fluid communication with said circulating fluid for removing air from said circulating fluid;
  wherein said catheter further comprises:
    an insulating chamber forming an outer portion of said catheter, said insulating chamber surrounding at least a portion of said first passageway an at least a portion of said second passageway, substantially before said first passageway and said second passageway connect to said inflatable thermal treating section, said insulating chamber containing a non-heated fluid, such that substantially only said inflatable thermal treating section is able to radiate heat sufficient to thermally ablate tissue.

26. The apparatus of claim 25, wherein the temperature of said non-heated fluid of said insulating chamber is substantially lower than said temperature of said fluid flowing through said first passageway and said second passageway.

27. The apparatus of claim 21, wherein said pump fixer features:

(i) a housing formed with:
(1) a substantially cylindrical cavity; and
(2) a lid, said lid having a depending shirt removably engageable within said cylindrical cavity;
(ii) a rotor rotatably mounted on a drive shaft within said cylindrical cavity, said rotor carrying rollers; and
(iii) a peristaltic tube connected to said tubular element, said peristaltic tube being engaged between said depending skirt and said rollers, such that a rotation of said rotor causes said fluid to flow from said peristaltic tube to said tubular element.

28. A closed loop thermal treatment apparatus for a body cavity, comprising:
(a) a catheter for insertion into the body cavity, said catheter being capable of receiving a quantity of circulating fluid;
(b) a temperature-setting device for setting a temperature of said circulating fluid being received by said catheter, said temperature-setting device comprising:
(i) a tubular element, said tubular element being attached to said catheter such that circulating fluid flows through said tubular element to said catheter; and
(ii) a transformer electrically connected to said tubular element, said transformer configured to supply power to said tubular element such that said tubular element heats the circulating fluid as the fluid flows therethrough; and
(c) a pump in fluid communication with said tubular element, said pump configured to drive said fluid through said tubular element; and
(d) an air trap in fluid communication with said circulating fluid for removing air from said circulating fluid, wherein said air trap comprises a plurality of valves, such that said fluid flows into said air trap substantially only when said valves are open, said valves being open substantially only when the apparatus is being primed.

29. The apparatus of claim 28, wherein said catheter, said air trap, said tabular element and said pump form a substantially closed system when the apparatus is being primed, and alternatively wherein said catheter, said tubular element and said pump form a substantially closed system after the apparatus has been primed.

30. A thermal treatment apparatus according to claim 1, wherein said tubular element of said temperature setting device is a single-use disposable element.

31. A thermal treatment apparatus according to claim 1, wherein said thermal apparatus is a closed loop system configured, in operation, to substantially continuously circulate between about 10–50 ml of thermally treated liquid.

32. A thermal treatment apparatus according to claim 10, wherein said tubular element and said insulating tubular elements are single-use disposable elements.

33. A thermal treatment apparatus according to claim 10, wherein said thermal apparatus is a closed loop system configured, in operation, to substantially continuously circulate between about 10–50 ml of thermally treated liquid.

34. A thermal treatment apparatus according to claim 21, wherein said tubular element of said temperature setting device is a single-use disposable element.

35. A thermal treatment apparatus according to claim 21, wherein said thermal apparatus is a closed loop system configured, in operation, to substantially continuously circulate between about 10–50 ml of thermally treated liquid.

* * * * *